United States Patent [19]
Fry

[11] Patent Number: 6,150,159
[45] Date of Patent: Nov. 21, 2000

[54] CELL CULTURE VESSEL

[75] Inventor: R. F. Fry, Clemency, Luxembourg

[73] Assignee: Cellon SA, Strassen, Luxembourg

[21] Appl. No.: 09/250,515

[22] Filed: Feb. 16, 1999

[30] Foreign Application Priority Data

Feb. 17, 1998 [GB] United Kingdom ............... 9803362

[51] Int. Cl.[7] .................................................. C12M 1/24
[52] U.S. Cl. .................................. 435/304.1; 435/298.2; 435/299.2
[58] Field of Search ........................... 435/288.1, 288.2, 435/298.1, 298.2, 304.1, 299.2, 304.2, 304.3; 422/102; 215/379, 380, 382

[56] References Cited

U.S. PATENT DOCUMENTS

| 3,221,878 | 12/1965 | Brett . | |
|---|---|---|---|
| 3,321,086 | 5/1967 | Dews et al. . | |
| 3,540,700 | 11/1970 | Freedman . | |
| 3,702,806 | 11/1972 | Oliva . | |
| 4,912,048 | 3/1990 | Smith et al. | 435/296 |
| 4,962,033 | 10/1990 | Serkes et al. | 435/240.243 |
| 5,139,952 | 8/1992 | Honda et al. | 435/284 |
| 5,151,366 | 9/1992 | Serkes et al. | 435/285 |
| 5,650,325 | 7/1997 | Spielmann . | |
| 5,672,484 | 9/1997 | Eden et al. . | |
| 5,866,419 | 2/1999 | Meder . | |

FOREIGN PATENT DOCUMENTS

| 89102547 | 2/1989 | European Pat. Off. . |
|---|---|---|
| 2 185 997 | 8/1987 | United Kingdom . |
| 2262 538 | 6/1993 | United Kingdom . |

Primary Examiner—William H. Beisner
Attorney, Agent, or Firm—Law Offices of Jane Massey Licata

[57] ABSTRACT

A cell culture vessel formed generally about an elongate axis and being provided with a neck and a removable closure member, and at a distal end thereof an end closure portion; said vessel being adapted for tissue culture growth and formed of a sterilizable plastics material, wherein the internal surface of the vessel is wettable for the attachment of cells; said vessel being characterized in that its cross-section in a direction perpendicular to said elongate axis is non-cylindrical whereby it cannot rotate smoothly by rolling on its surface(s).

5 Claims, 4 Drawing Sheets

CELL CULTURE VESSEL

The present invention relates to improvements in cell culture vessels.

EP-A-0 320 348 discloses a roller bottle for tissue culture. The roller bottle for tissue culture growth is formed of a clear, sterilizable synthetic resin wherein the inside surface of the bottle is treated to be wettable for attachment and growth of cells, comprising in combination:

a substantially cylindrical wall section having a central axis and comprising a pleated segment having a first edge and a second edge;

the pleated segment including from one to four unpleated axial panels to form a viewing panel for observing cells, a drain channel extending parallel to the central exosphere emptying the contents of the bottle and a plurality of pleats or corrugations disposed crosswise to the axis of the bottle, each of the pleats comprising an outer rim disposed in a common cylindrical plane and forming a circumferentially extending trough on the inside surface of the segment;

each of the panels being connected to said troughs and being disposed no nearer to said central axis than a common cylindrical plane and extending substantially from a first end to the second end of the cylindrical segment;

said roller bottle having an inner surface at least 110% the surface area of a roller bottle comprising an unpleated cylindrical segment having the same external diameter;

a top section of the bottle having a neck and closure connected to the first end of the cylindrical wall section; and a bottom section of the bottle connected to the second end of the cylindrical wall section.

In use, cells and liquid nutrients are aseptically introduced into the sterile roller bottle after removal of the roller bottle closure. The roller bottle is then sealed by replacing the closure over the neck of the bottle. The inside surface of each roller bottle then becomes coated with the cells. The cells are cultured by placing the roller bottle on two horizontal rollers whereby the central axis of the roller bottle is horizontal. The rollers rotate the bottle smoothly about its central axis for a specific length of time whereupon the bottle is manually or robotically emptied in aseptic conditions, by removing the closure from the neck of the roller bottle, draining the liquid nutrients and replacing them with new nutrients before replacing the closure. The roller bottle is then replaced on the rollers and culturing continues.

One disadvantage of this system is the requirement to manually or robotically drain and refill the bottle. This can take a significant amount of time and manpower which leads to significant coats if commercial production of, say, vaccines is occurring because there may be thousands of bottles to handle.

Another disadvantage is that to drain each bottle the cap must be removed for open processing, which can lead to contamination by air-borne microorganisms.

WO 96/05285 discloses a cell culture apparatus comprising a chassis or supporting frame, a rotor releasably housing a plurality of roller bottles, said rotor being mounted about a substantially horizontal axis or shaft supported by said frame, with means provided to facilitate rotation of the rotor at a controlled speed, a reversible multi-channel pump or pumps, mounted on and rotating with the rotor, a manifold with one or more sealable external connections and a plurality of connections communicating with the individual channels of the multi-channel pump or pumps; each of the roller bottles being equipped with a microporous air vent and a dip tube, the dip tube of each roller bottle being individually connected to one channel of said multi-channel pump or pumps, the arrangement of the parts being such that the assembly comprising the rotor, roller bottles, pump, manifold and the connections to the roller bottles may be rotated about said horizontal axis, and the arrangement also allowing fluid to be injected into or extracted from each roller bottle via a single external connection under the influence of said multi-channel pump or pumps.

Roller bottles which may be utilised with the aforementioned cell culture apparatus can be of the same configuration as those disclosed in EP-A-0 320 348.

The roller bottles used with the aforementioned cell culture apparatus are provided preassembled with a dip tube and a microporous air vent. This assembly, also with other components, is known as a bottle pack. One disadvantage of this is that the dip tube can be dislocated during handling and transportation. Thus when the bottle packs are inserted into the cell culture apparatus housing the dip tube will not be in the correct position relative to the drainage channel. If the dip tubes are dislocated they cannot be easily moved back to their optimum position for bottle drainage without the risk of compromising the sterility of the bottle. Having to relocate the dip tube also reduces the amount of time which should be saved by using the bottle packs.

The correct positioning of the bottle into the housing presently requires time and attention to detail. The bottles must be orientated in the housing so that when the cell culture apparatus stops to allow drainage, the bottles are orientated such that the drainage channel is at the bottom of the housing and the channel is at its lowermost part. As the roller bottles are circular in cross-section they can easily be initially placed in the wrong orientation. Even though they have been correctly placed in the housing and they are clamped in position it is possible that they may rotate about their horizontal axis even to a small degree, thus moving the relative position of said roller bottle. Therefore when a microprocessor stops the rotation of the cell culture apparatus at a predetermined time, the orientation of the drainage channel of some of the roller bottles will be in the wrong position relative to the lower most part of the bottle. This results in some of the cell culture medium being left in the roller bottle.

In this prior art a tilting mechanism is required with the cell culture apparatus to ensure that all the liquid nutrients can be removed from the bottle before pumping new liquid nutrients into it. Even when a tilting mechanism is provided not all of the liquid nutrient will be removed if, as described before, the dip tube or roller bottle has moved from its correct orientation. If the roller bottle has moved relative to the rotor assembly, part of the corrugated section of the bottle will form the lowermost part of the bottle. Thus during the tilting action some of the liquid nutrients will be trapped in the troughs produced by the corrugations of the bottle, preventing the liquid from being able to be pumped out of the bottle via the dip tube, which is only positioned to pump out liquid nutrients from the neck end of the roller bottle.

If the dip tube in the bottle becomes displaced relative to the drainage channel, the tip of the dip tube will no longer be positioned at the lowermost part of the bottle. In this situation all of the liquid nutrient which is below the tip of the dip tube will not be able to be pumped from the bottle via the dip tube.

There is, therefore, a need to provide a cell culture vessel which will ensure that the medium can be withdrawn and replaced without manual handling and preferably without tilting so that the correct operational orientation of the vessel can be readily determined.

According to a first aspect of the invention there is provided a cell culture vessel formed generally about an elongate axis and being provided with a neck, a removable closure member therefor, and at a distal end thereof an end closure portion; said vessel being adapted for tissue culture growth and formed of a sterilizable plastics material, wherein the internal surface of the vessel is wettable for the attachment of cells;

said vessel being characterized in that its cross-section in a direction perpendicular to said elongate axis is non-cylindrical whereby it cannot rotate smoothly by rolling on its surface(s).

In one embodiment the vessel further comprises at least one drainage channel which extends radially relative to the elongate axis of the vessel and has a point of maximum displacement adjacent one or both ends of the vessel. This ensures that the great majority of the liquid nutrient can be efficiently drained out. Preferably the drainage channel(s) extends circumferentially for up to 5% or 9° of the circumference of the cell culture vessel. This distance gives optimum drainage while ensuring that the optimum number of cells can be grown.

In a preferred embodiment a major portion of the drainage channel is parallel or slightly angled to the elongate axis of the cell culture vessel and adjacent one or either end of the vessel there is provided a radial extending well. The existence of these wells reduces the amount of liquid nutrient in the cell culture vessel after drainage, while also preventing dislocation of the dip tube tip during transport and handling and may obviate the requirement for tipping the vessel during voiding thereof.

In another embodiment there is provided a vessel comprising a major portion with a generally cylindrical configuration, but with a drainage channel in its circumferential periphery which channel extends radially outwardly relative to the elongate axis of the vessel and has a point of maximum depression adjacent the neck/and end closure portion. The drainage channel may extend only over a minor proportion of the length of the vessel if desired.

The drainage channel(s) may thus extend outwardly from the plane of the internal surface of the vessel so that the vessel cannot roll smoothly about its elongate axis. The drainage channel aids the operator as the orientation of the vessel relative to the dip tube is self apparent during the initial assembly of the apparatus; the drainage channel providing in effect a key that readily identifies the correct orientation of the vessel. As the vessel will not roll on its elongate axis the position of the vessel relative to the dip tube will not move during culture. Therefore when a microcprocessor stops the cell culture apparatus the vessel will be in the correct position to drain out the liquid nutrient.

Preferably the internal surface of vessel is corrugated. The corrugated internal surfaces increase the surface area of the cell culture vessel by up to 500%. Therefore more cells may potentially be grown per unit of area occupied by the culture vessel, which increases the efficiency of the process.

In a preferred embodiment the corrugated internal wall surface further comprises at least one non-corrugated panel which extends helically with respect to, parallel to, the elongate axis. Preferably the non-corrugated panel is either opposite the drainage channel or spaced from another non-corrugated panel, so as to stabilise the walls of the vessel. The non-corrugated panel may also act as a viewing panel so that the operator can view the inside of the cell culture vessel. In this respect, at least a section of the sterilisable plastics material is formed from a translucent plastics material. Preferably, the section corresponds to the non-corrugated panel.

Preferably the shape of a cross-section of the vessel is selected from an oval, an egg-shape, a triangle, a square, a rectangle, a pentagon or a hexagon. Where it is a right cylinder it will include a radially extending member, preferably a drainage channel.

The cell culture vessel of the invention is particularly useful when used with a cell culture apparatus as disclosed in WO96/05285. Such a cell culture apparatus comprises a supporting frame, a rotor releasably housing a plurality of cell culture vessels, said rotor being mounted about a substantially horizontal axis or shaft supported by said frame with means provided to facilitate rotation of the rotor at a controlled speed, a reversible multi-channel pump or pumps mounted on and rotating with the rotor, a manifold with at least one sealable external connection and a plurality of connections communicating with the individual channels of the multi-channel pump or pumps, each of the cell culture vessels being equipped with a microporous air vent and a dip tube, the dip tube of each vessel being individually connected to one channel of said multi-channel pump or pumps, the arrangement of the parts being such that the assembly comprising the rotor, cell culture vessels, pump, manifold and the connections to the cell culture vessels may be rotated about said horizontal axis, the arrangement also allowing fluid to be injected into or extracted from each cell culture vessel via a single external connection, under the influence of said multi-channel pump or pumps.

The cell culture vessels for use with this arrangement may be provided with a cross-section in a direction perpendicular to the cell culture vessel's elongate axis that is non-right cylindrical whereby it cannot rotate by rolling on its right cylindrical surface.

Most preferably the housing and vessels are adapted to interfit. If the housing and the cell culture vessels of the invention are adapted to interfit then the cell culture vessels will not require clamps to stop the rotating within the housing. Preferably the cell culture vessels can only fit into the housing in one orientation and may include a formation on the vessel which tends to secure the vessel in situ in the housing. Such a formation may be a clip portion or other portion formed integrally with the vessel adapted to this end.

Thus the cell culture vessels of the invention will be initially inserted in the correct position for drainage and will not change their relative orientation during rotation. Therefore after rotation they will be in the same position and no relative adjustment will be needed before extraction of the liquid medium.

Conveniently the vessels are corrugated with drainage channel(s) which extend radially outward relative to the elongate axis of the vessel; having a point of maximum relative displacement adjacent both end portions of the vessel e.g. at the neck and/or end closure portion whereby when initially connected to the cell culture apparatus, the drainage channel is disposed at the tip of the dip tube(s). If the dip tube tips are disposed at a position relative to the drainage channel at the initial connection of the vessel to the cell culture apparatus and the vessel cannot move during culturing, then when the culturing process is stopped by the microprocessor in order that the medium may be pumped out, a maximum amount of the medium will be pumped out because none will be trapped. The cell culture apparatus need not have a tilting mechanism when the drainage channels are relatively sloped or angled because the medium will collect adjacent the neck or end closure portions where the dip tube terminates, especially if well portions are provided adjacent relative end portions of the vessel e.g. at the neck and end closure portions.

Preferably the drainage channels extend radially with respect to the circumference of the cell culture vessel for up to 5% of 9° of the circumference of said vessel. Therefore when a dip tube is placed in the drainage channel it can only move approximately 4.5° in a clockwise or anti-clockwise direction. During handling and transportation the dip tubes will remain in relatively the same position and therefore during assembly of the culture vessel into the rotor housing assembly no adjustment to the dip tube(s), which may compromise the sterility of the cell culture vessel, will be required.

In a preferred embodiment the injection or extraction of fluid is adapted to be effected aseptically without removal of the vessel or a closure member associated therewith. To this end, the end cap may be screw threaded and may be positioned either axially or at any other convenient position.

According to a second aspect of the invention there is provided an elongate cell culture vessel having a hollow body portion formed of a sterilizable plastics material and shaped externally to resist rolling, a major portion of said body portion being formed with corrugations to present an increased surface area internally of said vessel for culture growth; the body portion being further formed with a drainage channel running longitudinally of said vessel, intersecting said corrugations and defining a drainage location for liquid in the vessel; the drainage channel extending outwardly of the remainder of the body portion at least in the vicinity of said drainage location, providing a key indicative of a desired operational orientation for the vessel.

The invention will now be described, by way of illustration only, with reference to the following examples and the accompanying figures.

Figure 1:
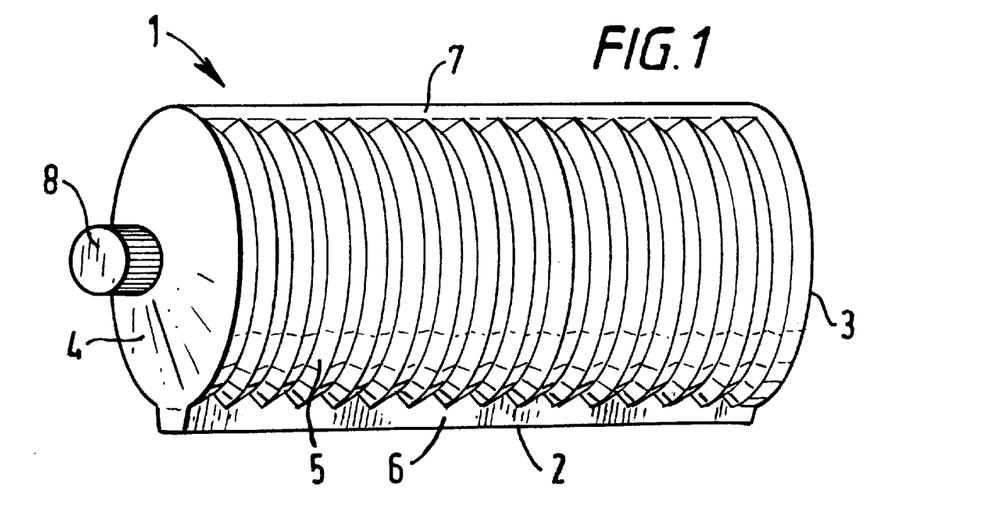
FIG. 1 is a corrugated oval culture vessel with a drainage channel.

FIG. 1 shows one embodiment of this invention. A cell culture vessel 1, which is produced from a clear sterilizable plastics material, has a generally oval cross section perpendicular to its elongate axis (shown in FIG. 2). The cell culture vessel 1 comprises a body portion 2 with a base portion 3 and a neck portion 4 provided with an end cap 8. The base portion 3 is opposite the neck portion 4 along the elongate axis of the body portion 2. The body portion 2 comprises a circumferentially corrugated portion 5, a non-corrugated drainage channel 6 and a non-corrugated panel 7. The corrugations in the inner surface of the body portion 2 provide up to 150% more surface area on the inner surface of the cell culture vessel 1 than if a non-corrugated vessel was used. The non-corrugated drainage channel 6 is disposed opposite the non-corrugated panel 7 along the major axis of the oval cross-section. The non-corrugated panel 7 provides a viewing panel for the operator. It is easier for the operator to view the growing cells through a flat non-corrugated panel that it is to view them through the corrugated sections. Together the drainage channel 6 and the non-corrugated panel 7 add stability to the corrugated body of the cell culture vessel since the presence of the non-corrugated areas means that the body will not collapse in a concertina like fashion.

The drainage channel 6 allows liquid nutrient in the cell culture vessel to be emptied with minimal retention due to retention caused by the corrugations. In addition the drainage channel 6 extends downwardly relative to the elongate axis of the vessel 1 and has a point of maximum radial depression adjacent the neck portion 4. The neck portion 4 may be formed integrally with a closure member or may comprise a screwthread portion (not shown) which can be sealed with a removable closure 8. The screwthread portion allows cells and liquid nutrient to be placed in and removed from the cell culture vessel 1 without the use of pumps etc. The closure 8 seals the cell culture vessel 1 so that the liquid nutrient (not shown) cannot leak out during the culturing process. The closure 8 also makes an air tight seal and so also reduces the likelihood of contamination of the cells and the liquid nutrient during culturing.

Figure 2:
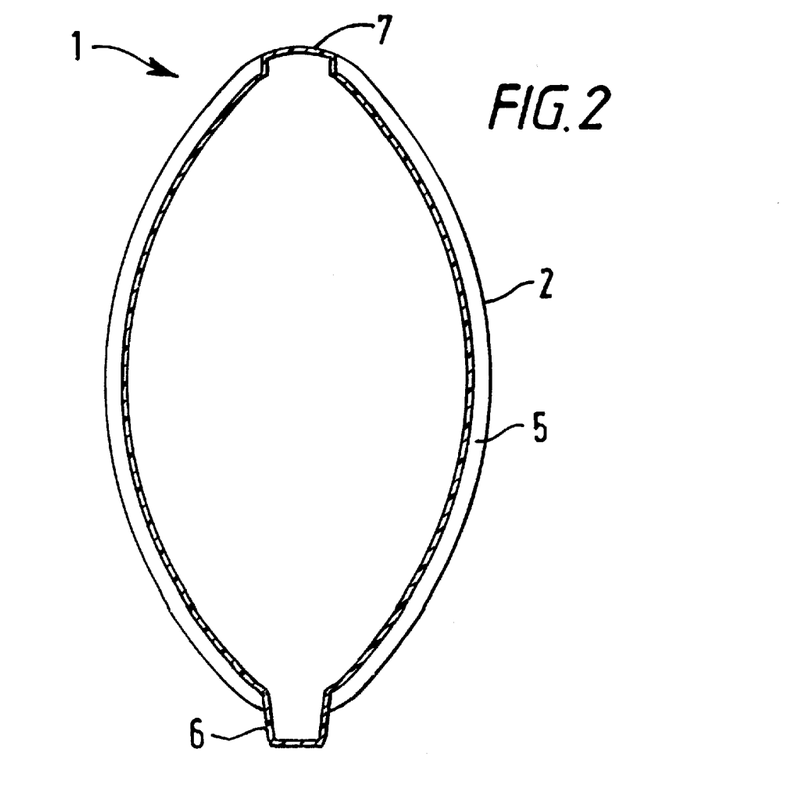
FIG. 2 is a transverse cross-section of the corrugated cell culture vessel with a drainage channel shown in FIG. 1.

In FIG. 2 the body portion 2, of the cell culture vessel 1 has a generally oval transverse cross section and comprises a corrugated portion 5, a drainage channel 6 and a non-corrugated panel 7 as described above.

Figure 3:
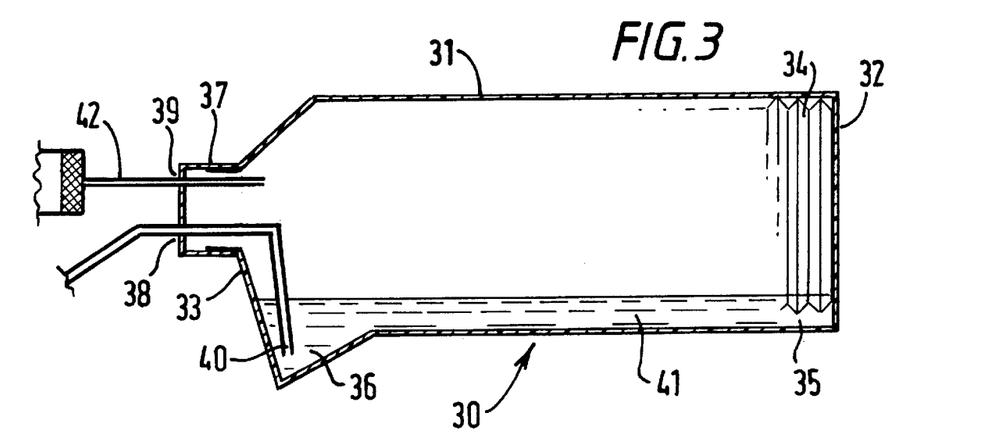
FIG. 3 is a vertical cross section of a corrugated cell culture vessel with a drainage channel.

Alternative embodiments of the cell culture vessel are shown in FIGS. 3 7, 8 and 9. They can be used in conjunction with the apparatus shown in FIG. 6. With reference to FIG. 3, the cell culture vessel 30, which is formed from a clear sterilizable plastics material, comprises a body portion 31, and end portion 32 and a neck portion 33. The end portion 32 is located at the opposite end of the elongate axis of the body portion 31 to the neck portion 33. This gives the vessel a generally cylindrical shape. The body portion 31 further comprises a corrugated body portion 34 and a non-corrugated drainage channel 35. A major portion of the non-corrugated drainage channel 35 extends along the cell culture vessel 30 from the end portion 32 to the neck portion 33, parallel to the elongate axis of the cell culture vessel. Adjacent the neck portion 33 a drainage channel 35 is displaced relatively radially outwardly to from a well 36.

The closure 37 is formed with two outlets. The first outlet 38 accommodates a dip tube 30 and the second outlet 39 forms a microporous air vent 42. The first outlet 38 accommodates dip tube 40, the tip of which sits in the well 36. As the tip of tube 40 is placed in the well 36 it resists movement during handling or transportation of the cell culture vessel. As all the liquid nutrients 41 will pour into the well during pumping out through the dip tube 40, minimal liquid nutrient 41 is retained in cell culture vessel 30 after pumping out. The microporous air vent 39 filters out air-borne microorganisms but allows air in and out to equilibrate the pressure in the cell culture vessel 30 during the process of changing the liquid nutrients.

Figure 4:
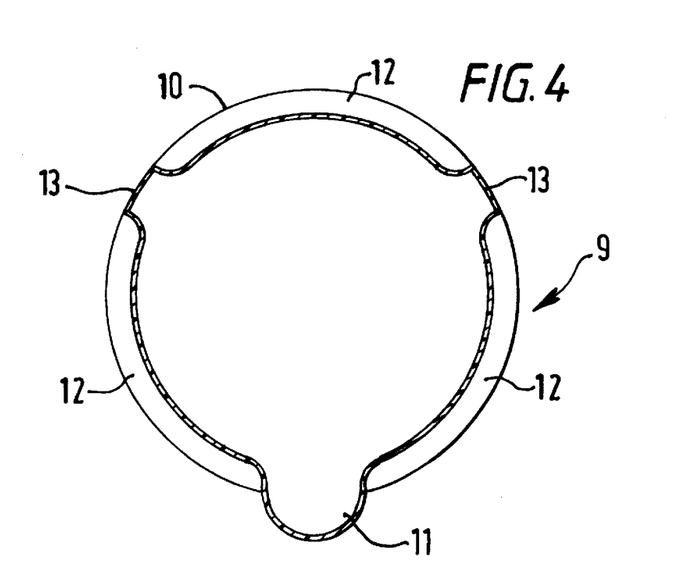
FIG. 4 is a transverse cross-section of a corrugated cell culture vessel which has a major portion of the body cylindrical with a drainage channel which extends downwardly relative to the elongate axis of the vessel and having a point of maximum depression adjacent the neck portion.
Figure 5:
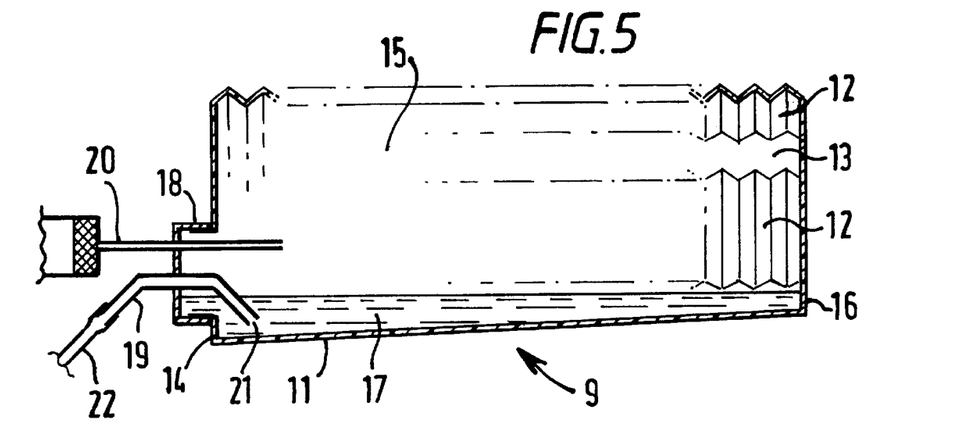
FIG. 5 is a vertical cross-section of the transverse section of the cell culture vessel shown in FIG. 4. It has a dip tube and microporous air vent for use with the cell culture apparatus in FIG. 6.

An alternative embodiment is shown in FIG. 4, the transverse cross section of the cell culture vessel 9, which is produced from a clear sterilizable plastics material, comprises a generally right cylindrical portion 10 with an arcuate drainage channel 11 which extends radially outwardly relative to the elongate axis of the vessel and has a point of maximum displacement adjacent a neck portion 14 (shown in FIG. 5). The cylindrical portion comprises three circumferentially orientated corrugated portions 12 and two elongate non-corrugated viewing panels 13 which are placed equidistant from the arcuate drainage channel 11 and extend generally in parallel to the elongate axis of the cylindrical portion 10. It will be seen that the channel 11 positioned at its lowermost point, liquid will collect therein.

Figure 6:
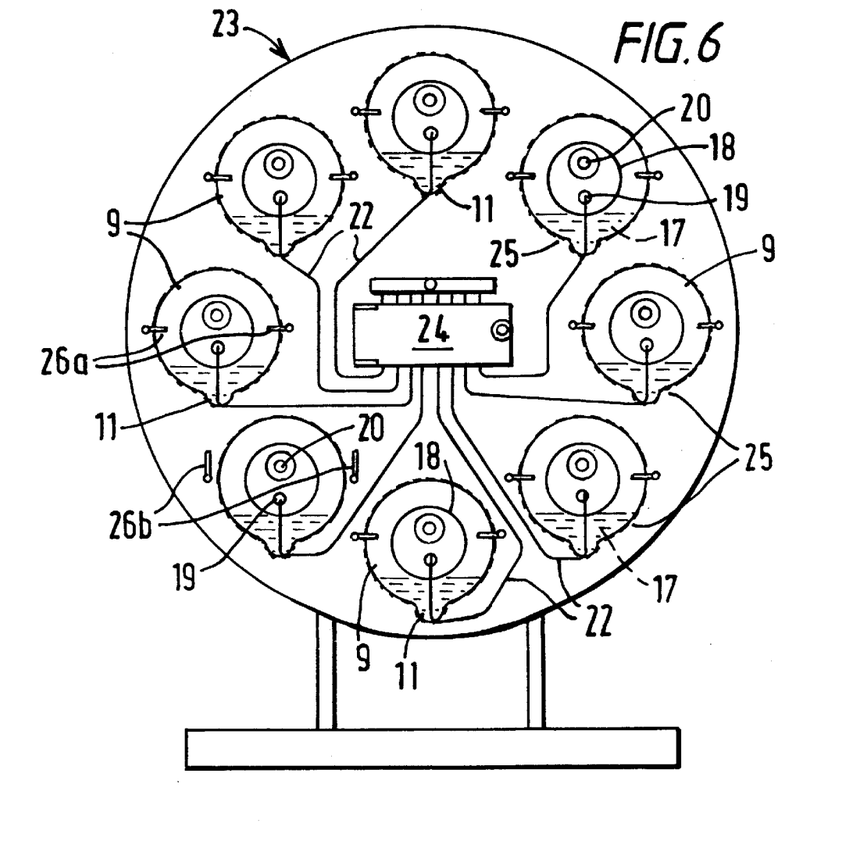
FIG. 6 is a diagrammatic representation of the cell culture apparatus for use with the cell culture vessels represented in FIGS. 1 to 5.

The embodiment shown in FIG. 5 shows a cell culture vessel 9 similar to that of FIG. 3 for use in conjunction with a cell culture apparatus 18 shown in FIG. 6. The cell culture vessel 9, which is formed from clear sterilizable plastics material, comprises a body portion 15, an end portion 16 and the neck portion 14. The end portion 16 is located at the opposite end of the elongate axis of the body portion 15 to the neck portion 14. The body portion further comprises the corrugated body portion 12, the non-corrugated viewing panel 13 and the arcuate drainage channel 11. The corrugated body portion 12 is split into segments by the non-corrugated panel 13 and the drainage channel 11. A second viewing panel (not shown) is placed about 60° from the arcuate drainage channel 11 on the opposite side of the cell culture vessel 9 to that shown.

The body portion 15 and the arcuate drainage channel 11 may contain liquid medium 17. The arcuate drainage channel 11 is angled downwardly relative to the elongate axis of the vessel from the end portion 16 to the neck portion 14. The neck portion comprises a screwthread portion (not shown). The screwthread portion is shaped to interfit with a closure 18. The closure 18 comprises a dip tube 19 and a microporous air vent 20. The dip tube 19 has a tip 21 located in the drainage channel 11 adjacent the neck portion 14. At the opposite end of the dip tube 19 to the tip 21 is a section of pump tube 22. The pump tube 22 joins the dip tube 19 to a pump 24 (see FIG. 6).

From a reservoir of liquid nutrient (not shown) the pump 24 initially injects a specific amount of liquid nutrient 17 into the cell culture vessel 9. After culturing the pump drains the liquid nutrient out from the cell culture vessel and replaces it with new liquid nutrient. The specific amount of liquid nutrient injected into the cell culture vessel 9 depends upon the instructions programmed into the microprocessor (not shown) which operates the apparatus of FIG. 6. As the drainage channel 11 slopes relatively downwardly towards the neck portion 14 this aids removal of all the liquid nutrient 17 during the pumping process. The microporous air vent 20 works as described before in FIG. 3.

The cell culture apparatus 23 shown in FIG. 6 houses a plurality of cell culture vessels 9. The drainage channels 11 are directed downwardly relative to the bottom of a housing 25. The housing 25 is not symmetrical about its horizontal axis because there has to be extra space in the lower portion of the housing 25 for the drainage channel 11. The asymmetry of the cell culture vessel 9 about its horizontal axis (when taking in the same orientation as the cell culture apparatus) means that the cell culture vessel 9 can only be located in the housing 25 in one orientation. This aids the operator and reduces the time it takes to assemble the cell culture apparatus 23 with the cell culture vessels 9. As the housing 25 interfits with the cell culture vessel 9 the latter cannot rotate in the housing 25 during culturing. Thus when a microprocessor (not shown) stops rotating the cell culture apparatus 25, so that the liquid nutrient 17 may be pumped out through the dip tube 19, the dip tube 19 will be in the correct orientation relative to the drainage channel 11. The cell culture vessels 9 will not rotate in the housing 25 however as shown in this embodiment it may be expedient to provide two clamps 26a/b to ensure the culture vessel 9 does not slide out of the housing 25. The two clamps 26a/b are disposed on opposite sides of the housing to each other. In their engaged position the clamps 26a are positioned over the neck portion of the bottle to stop it sliding out of the housing 25. In their stowed position the clamps 26b are positioned away from the front of the housing so that the cell culture vessel 9 can easily be slipped in or out. To engage the clamps 26b they must be turned in a clockwise or anticlockwise direction.

As described above the microporous air vent 20 allows air to enter the cell culture vessel 9 while the pump 24 is pumping liquid nutrient 17 out of the cell culture vessel 9 via the dip tube 19. When the pump 24 is adding nutrients to the cell culture vessel 9 the microporous air vent 20 works in reverse and allows air to leave the cell culture vessel 9.

Figure 7:
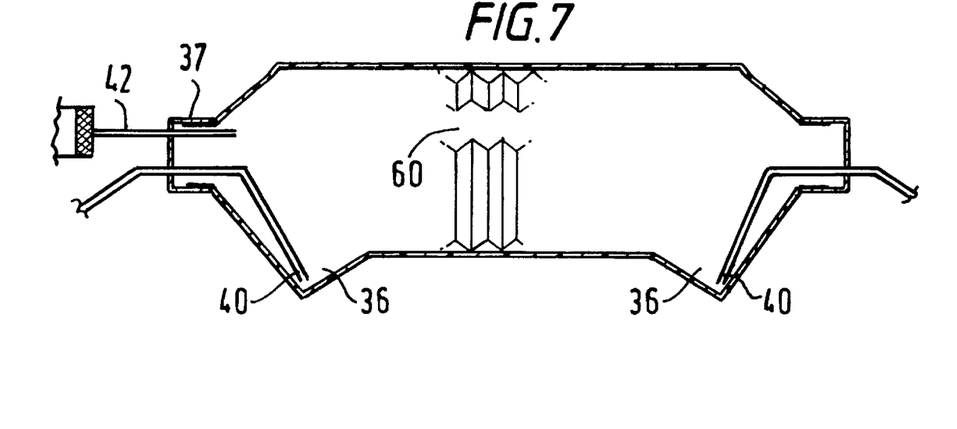
FIG. 7 shows a vertical cross-section of a corrugated cell culture vessel with a drainage channel at each end.
Figure 8:
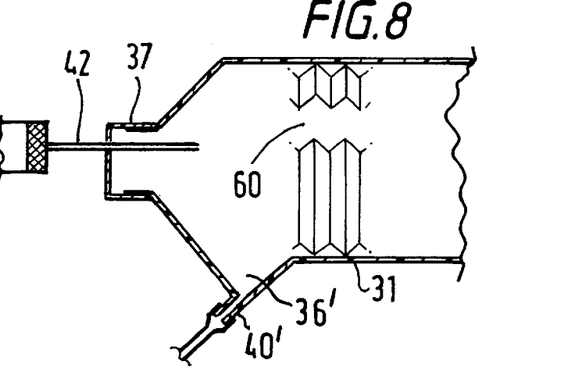
FIG. 8 shows in transverse cross section of an end of a corrugated cell culture vessel with a fixed drainage channel.
Figure 9:
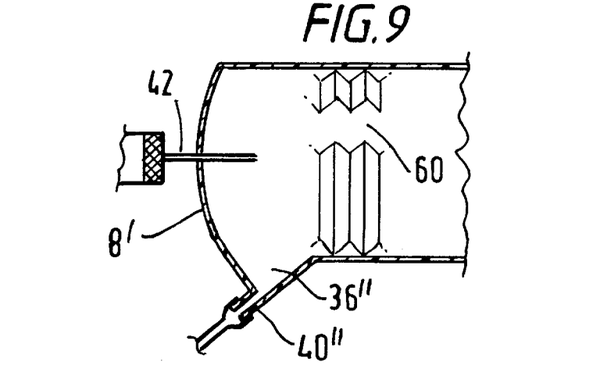
FIG. 9 shows an arrangement of FIG. 8 wherein the end cap has been displaced.

Turning now to FIGS. 7, 8 and 9, these represent alternatives particularly to that shown in FIG. 3. Like numbering in FIGS. 7, 8 and 9 to that used in FIG. 3 shows that these figures are similar but differ in various ways.

FIG. 7 differs from FIG. 3 in that both ends of the vessel 50 are formed with radially outwardly extending drainage channels 36 with attendant dip tubes 40. This arrangement while it complicates pumping arrangements, facilitates drainage and down-times, and may enable the system to be used in perfusion mode.

FIG. 8 shows drainage tube 40' extending from well 36' so that only the vent 42 is required in the closure 37. The closure 37 maybe dispensed with in FIG. 9 which shows that the vent 42 passes through the body 31 at a convenient position; here axially. Drainage tube 40" extends from well 36".

In order to enhance the surface area of the vessel shown in FIGS. 7, 8 and 9 the body of the vessel is corrugated with a generally planar non-corrugated viewing panel 60.

Although not often required reference 8' indicates a position at which a closure of the form described above may be provided to suit certain requirements.

In other embodiments cell culture vessels with different cross sections perpendicular to their elongate axis can be utilised, for example pentagons or hexagons.

What is claimed is:

1. A cell culture vessel formed generally about an elongate axis and being provided with a neck and a removable closure member, and at a distal end thereof an end closure portion; said vessel being adapted for tissue culture growth and formed of a sterilizable plastics material, wherein the internal surface of the vessel is wettable for the attachment of cells; said vessel being characterized in that its cross-section in a direction perpendicular to said elongate axis is non-cylindrical whereby it cannot rotate smoothly by rolling on its surface(s);

wherein the vessel further comprises a drainage channel which extends radially outwardly relative to the elongate axis of the vessel and has a point of maximum displacement adjacent to either or both ends of said vessel;

wherein a major portion of the drainage channel is generally parallel to the elongate axis of the cell culture vessel and wherein a radially outwardly formed well is disposed adjacent at least one end portion of the vessel; and wherein the internal surface of the vessel is corrugated.

2. A cell culture vessel according to claim 1 wherein the corrugated internal wall surface further comprises at least one non-corrugated panel which extends helically or parallel to the elongate axis.

3. A cell culture vessel according to claim 1 wherein the shape of the cross-section or the vessel is selected from an oval, an egg-shape, a triangle, a square, a rectangle, a pentagon a hexagon and generally a right cylinder but with a radially outwardly extending drainage channel thereon.

4. An elongate cell culture vessel having a hollow body portion formed of a sterilizable plastics material and shaped externally to resist rolling, a major portion of said body portion being formed with corrugations to present an increased surface area internally of said vessel for culture growth; the body portion being further formed with a drainage channel running longitudinally of said vessel, intersecting said corrugations and defining a drainage location for liquid in the vessel; the drainage channel extending outwardly of the remainder of the body portion at least in the vicinity of said drainage location, providing a key indicative of a desired operational orientation for the vessel.

5. A cell culture vessel formed generally about an elongate axis and being provided with a neck and a removable closure member, and at a distal end thereof an end closure portion; said vessel being adapted for tissue culture growth and formed of a sterilizable plastics material, wherein the internal surface of the vessel is wettable for the attachment of cells; said vessel being characterized in that its cross-section in a direction perpendicular to said elongate axis is non-cylindrical whereby it cannot rotate smoothly by rolling on its surface(s);

wherein the vessel further comprises a drainage channel which extends radially outwardly relative to the elongate axis of the vessel and has a point of maximum displacement adjacent to either or both ends of said vessel;

wherein a major portion of the drainage channel is generally parallel to the elongate axis of the cell culture vessel and wherein a radially outwardly formed well is disposed adjacent at least one end portion of the vessel; and wherein the shape of the cross-section of the vessel is selected from an oval, an egg-shape, a triangle, a square, a rectangle, a pentagon, a hexagon and generally a right cylinder but with a radially outwardly extending drainage channel thereon.

* * * * *

UNITED STATES PATENT AND TRADEMARK OFFICE
CERTIFICATE OF CORRECTION

PATENT NO. : 6,150,159
DATED : November 21, 2000
INVENTOR(S) : Fry

It is certified that error appears in the above-identified patent and that said Letters Patent are hereby corrected as shown below:

Col. 6, line 56, please delete "30" and insert therefor --40--

Signed and Sealed this

First Day of May, 2001

Attest:

NICHOLAS P. GODICI

*Attesting Officer*     Acting Director of the United States Patent and Trademark Office